United States Patent [19]

Morgan

[11] Patent Number: 4,533,655

[45] Date of Patent: Aug. 6, 1985

[54] ANALGESIC DIPEPTIDE AMIDES AND METHOD OF USE AND COMPOSITIONS THEREOF

[75] Inventor: Barry A. Morgan, Albany, N.Y.

[73] Assignee: Sterling Drug Inc., New York, N.Y.

[21] Appl. No.: 423,138

[22] Filed: Sep. 24, 1982

Related U.S. Application Data

[63] Continuation-in-part of Ser. No. 286,672, Jul. 24, 1981, abandoned.

[51] Int. Cl.$^3$ .................... A61K 37/00; C07C 103/52
[52] U.S. Cl. .................................... 514/18; 514/809; 260/112.5 R
[58] Field of Search ................. 260/112.5 R; 424/177

[56] References Cited

U.S. PATENT DOCUMENTS 4,127,535  11/1978  Coy et al. .................... 260/112.5 R

OTHER PUBLICATIONS

Shinagawa et al., Chem. Pharm. Bull., vol. 29, No. 12, pp. 3639–3645, 1981.
McGregor et al., Life Sciences, vol. 23, No. 13, pp. 1371–1376, 1978.
Roques et al., European Journal of Pharmacology, vol. 60, pp. 109–110, 1979.
Peptides, 2 (3), 305–307, (1981).
Peptide Chemistry, (1981), 65–68.

*Primary Examiner*—Delbert R. Phillips
*Attorney, Agent, or Firm*—Theodore C. Miller; Paul E. Dupont; B. Woodrow Wyatt

[57] ABSTRACT

A genus of dipeptide amides including as the preferred subgenus the dipeptide amides having the structural formula $R_1TyrR_2D$-$AlaNHR_4$ wherein $R_1$ and $R_2$ are each hydrogen or alkyl provided that at least one of them is other than hydrogen and $R_4$ is phenylalkyl or substituted-phenylalkyl are prepared by condensing the dipeptide with the amine or the amino acid with the amino acid amide and are useful as analgesics.

18 Claims, No Drawings

ANALGESIC DIPEPTIDE AMIDES AND METHOD OF USE AND COMPOSITIONS THEREOF

CROSS-REFERENCE TO RELATED APPLICATION

This application is a continuation-in-part of my co-pending application Ser. No. 286,672 filed July 24, 1981, and now abandoned.

BACKGROUND OF THE INVENTION

1. Field of the Invention

The invention relates to dipeptide amides which are useful as analgesics.

2. Description of the Prior Art

Coy and Kastin U.S. Pat. No. 4,127,535 describes

H-Tyr-X-Y wherein: X is a chiral residue of a D-amino acid selected from the group consisting of D-alanine, D-leucine, D-isoleucine, D-valine, D-phenylalanine, D-tyrosine, D-trytophan, D-serine, D-threonine, D-methionine, D-glutamic acid, D-glutamine, D-proline[,] D-aspartic acid, D-asparagine, D-lysine, D-arginine and D-histidine; and Y is selected from the group consisting of hydroxy, amino, loweralkylamino, diloweralkylamino and lower alkoxy which are stated to be useful as analgesic, tranquilizer, sedative, hypnotic, anti-depressant[,] prolactin releasing and growth hormone releasing agents and which are designated in the illustrative examples as derivatives of β-lipotropin fragment 61–62. Example 34 specifically describes D-Ala²-β-lipotropin fragment 61–62 amide by name and method of preparation but does not describe any chemical or biological properties thereof.

McGregor (et al., Life Sciences, vol. 23, no. 13, pp. 1371–1378, 1978) describes H-Tyr-D-Ala-NH$_2$ (D-Ala²-β-lipotropin fragment 61–62) and shows that it is greater than 10 times less potent intravenously and 200 times less potent intraventricularly in the tail flick test for analgesia in the rat, and binds to the opiate receptor in rat brain membranes with 830 times less affinity, than morphine.

Roques (et al., European Journal of Pharmacology, vol. 60, pp. 109–110, 1979) describes HTyrD-AlaNH(CH$_2$)$_2$NH(CH$_2$)$_2$Phenyl, which was less then 1% as potent as Met-enkephaline in both the guinea pig ileum and mouse vas deferens tests.

SUMMARY OF THE INVENTION

In a composition of matter aspect the invention is 2-(L-N$^2$-R$_1$-N-R$_2$-tyrosylamino)-2-R$_3$-N-R$_4$-acetamide having the structural formula

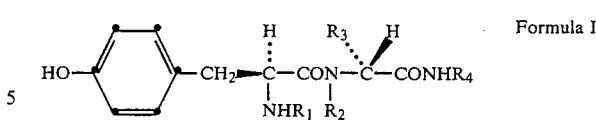

Formula I wherein
- R$_1$ is hydrogen, alkyl of one to five carbon atoms, allyl, cyclopropylmethyl, formyl, acetyl or propionyl; and
- R$_2$ is hydrogen or alkyl of one to five carbon atoms; provided that at least one of R$_1$ and R$_2$ is other than hydrogen;
- R$_3$ is alkyl of one to five carbon atoms; and
- R$_4$ is (CH$_2$)$_n$Y, wherein n is an integer from 2 through 10 and Y is phenyl or phenyl substituted by fluoro, chloro, methyl, methoxy or trifluoromethyl;

or a pharmaceutically acceptable acid addition salt thereof.

The compounds of Formula I are useful as analgesics.

In a first process aspect the invention is the process of preparing 2-(L-N$^2$-R$_1$-N-R$_2$-tyrosylamino)-2-R$_3$-N-R$_4$-acetamide of Formula I which comprises condensing the corresponding L-N-R$_1$-tyrosine with the corresponding 2-R$_2$NH-2-R$_3$-acetic acid to form the corresponding 2-(L-N$^2$-R$_1$-N-R$_2$-tyrosylamino)-2-R$_3$-acetic acid and then condensing said 2-(L-N$^2$-R$_1$-N-R$_2$-tyrosylamino)-2-R$_3$-acetic acid with the corresponding H$_2$NR$_4$, concomitantly protecting and deprotecting the α-amino, tyrosyl phenolic hydroxyl and acetyl carboxyl groups as required.

In a second process aspect the invention is the process of preparing 2-(L-N$^2$-R$_1$-N-R$_2$-tyrosylamino)-2-R$_3$-N-R$_4$-acetamide of Formula I which comprises condensing the corresponding L-N-R$_1$-tyrosine with the corresponding 2-R$_2$NH-2-R$_3$-acetic acid methyl ester to form the corresponding 2-(L-N$^2$-R$_1$-N-R$_2$-tyrosylamino)-2-R$_3$-acetic acid methyl ester, then condensing said 2-(L-N$^2$-R$_1$-N-R$_2$-tyrosylamino)-2-R$_3$-acetic acid methyl ester with hydrazine to form 2-(L-N$^2$-R$_1$-N-R$_2$-tyrosylamino)-2-R$_3$-acetyl hydrazide, then reacting said 2-(L-N$^2$-R$_1$-N-R$_2$-tyrosylamino)-2-R$_3$-acetyl hydrazide with an alkyl nitrite to form 2-(L-N$^2$-R$_1$-N-R$_2$-tyrosylamino)-2-R$_3$-acetyl azide, then condensing said 2-(L-N$^2$-R$_1$-N-R$_2$-tyrosylamino)-2-R$_3$-acetyl azide with the corresponding H$_2$NR$_4$, concomitantly protecting and deprotecting the α-amino and tyrosyl phenolic hydroxyl groups as required.

In a third process aspect the invention is the process of preparing 2-(L-N$^2$-R$_1$-N-R$_2$-tyrosylamino)-2-R$_3$-N-R$_4$-acetamide of Formula I which comprises condensing the corresponding 2-R$_2$NH-2-R$_3$-acetic acid with the corresponding H$_2$NR$_4$ to form the corresponding 2-R$_2$NH-2-R$_3$-N-R$_4$-acetamide and then condensing said 2-R$_2$NH-2-R$_3$-N-R$_4$-acetamide with L-N-R$_1$-tyrosine, concomitantly protecting and deprotecting the α-amino and tyrosyl phenolic hydroxyl groups as required.

In a method of use aspect the invention is the method or producing analgesia in a mammal in pain which comprises administering to the mammal an analgesically effective amount of 2-(L-N$^2$-R$_1$-N-R$_2$-tyrosylamino)-2-R$_3$-N-R$_4$-acetamide of Formula I or a pharmaceutically acceptable acid addition salt thereof.

In another composition of matter aspect the invention is a pharmaceutical composition for producing analgesia in a mammal consisting essentially of an analgesically effective concentration of 2-(L-$N^2$-$R_1$-N-$R_2$-tyrosylamino)-2-$R_3$-N-$R_4$-acetamide of Formula I or a pharmaceutically acceptable acid addition salt thereof and a pharmaceutically acceptable vehicle.

When $R_1$, $R_2$ or $R_3$ of Formula I is alkyl of one to five carbon atoms, it can be any of the possible primary, secondary and tertiary alkyls of one to five carbon atoms, especially including methyl, ethyl, n-propyl, isopropyl, n-butyl, tert-butyl, n-pentyl and 3-methylbutyl.

In a preferred composition of matter aspect the invention is N-$R_1$-L-tyrosyl-$N^2$-$R_2$-N-$R_4$-D-alaninamide having the structural formula $R_1$TyrR$_2$D-AlaNHR$_4$    Formula II, which is the compound of Formula I wherein $R_3$ is methyl, or a pharmaceutically acceptable acid addition salt thereof.

In a most preferred composition of matter aspect the invention is the following compounds of Formula II, which are the free base forms of the compounds of the examples whose preparation and biological properties are described below.

| Compound of Formula II | Example |
|---|---|
| HTyrMeD-AlaNH(CH$_2$)$_3$Ph | 1 |
| MeTyrD-AlaNH(CH$_2$)$_3$Ph | 2 |
| MeTyrMeD-AlaNH(CH$_2$)$_3$Ph | 3 |
| HTyrEtD-AlaNH(CH$_2$)$_3$Ph | 4 |
| HTyrMeD-AlaNH(CH$_2$)$_3$PhCl-p | 5 |
| HTyrMeD-AlaNH(CH$_2$)$_3$PhCF$_3$-p | 6 |
| HTyrMeD-AlaNH(CH$_2$)$_3$PhF-p | 7 |

In Formula II and the foregoing formulas of specific compounds of Formula II
Tyr represents L-tyrosyl,
D-Ala represents D-alanyl,
Me represents methyl,
Et represents ethyl,
Ph represents phenyl,
PhF-p represents p-fluorophenyl,
PhCl-p represents p-chlorophenyl, and
PhCF$_3$-p represents p-trifluoromethylphenyl, The symbols Tyr and D-Ala do not include the N-terminal and C-terminal groups. H of HTyr or Me of MeTyr is the same as $R_1$ of Formula I when $R_1$ is hydrogen or methyl, Me of MeD-Ala or Et of EtD-Ala is the same as $R_2$ of Formula I when $R_2$ is methyl or ethyl, and $R_1$, $R_2$ and $R_4$ are otherwise also the same as $R_1$, $R_2$ and $R_4$ of Formula I.

DETAILED DESCRIPTION OF THE INVENTION INCLUSIVE OF THE PREFERRED EMBODIMENTS

Preparation of the Compounds

The protection, activation, condensation and deprotection steps required to prepare the compounds of Formula I are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and dipeptide intermediates can be formed and used with or without being isolated and include the acyl halides and pseudohalides, especially the acyl azides; the anhydrides, especially the mixed anhydrides and most especially the mixed anhydride with diphenylphosphinyl chloride, isobutyl chloroformate or pivalyl chloride; derivatives formed by addition reactions, especially using dicyclohexylcarbodimide; displaceable acyl derivatives of heterocyclic nitrogen; ring-openable activated heterocyclic systems; acylphosphonium derivatives; activated esters, especially N-hydroxysuccinimide, nitrophenyl and pentafluorophenyl esters; and polymeric (solid phase) derivatives.

It is necessary that the N-terminal α-amino function be protected during the amide forming steps. It is preferred but not essential that the tyrosyl phenolic hydroxyl also be protected. The preferred α-amino protecting groups are benzyloxycarbonyl (Z), which can be removed by catalytic hydrogenation using palladium as catalyst or by hydrogen bromide in acetic acid, and tert-butyloxycarbonyl (Boc), which can be removed by acidic cleavage, for example, with hydrogen chloride in a suitable solvent or trifluoroacetic acid. Benzyl (Bz) and tert-butyl (tBu) are the preferred tyrosyl phenolic hydroxyl protecting groups. Benzyl can be removed by catalytic hydrogenation using palladium as catalyst or by hydrogen bromide in acetic acid. tert-Butyl can be removed by acidic cleavage, for example, with hydrogen chloride in a suitable solvent or trifluoroacetic acid.

The C-terminal carboxyl group must be protected during the peptide forming step. In the first process aspect it is protected as the amide, which is, of course, not removed. In the second process aspect the methyl ester protects the carboxyl group during peptide bond formation and subsequently activates it for hydrazide bond formation. In the third process aspect the C-terminal carboxyl group can be protected as the carboxylate salt, the t-butyl ester, which can be removed by acidic cleavage, for example, with hydrogen chloride in a suitable solvent or trifluoroacetic acid, or the benzyl ester, which can be removed by catalytic hydrogenation using palladium as catalyst.

The unprotected and protected L-N-$R_1$-tyrosine, unprotected and protected 2-$R_2$NH-2-$R_3$-acetic acid, 2-$R_2$NH-2-$R_3$-acetic acid methyl ester and H$_2$NR$_4$ starting materials are known classes of compounds. The individual compounds are commercially available or can be made by methods specifically or generally described in the chemical literature.

The acid addition salts of the compounds of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formula I and the acid addition salts thereof are hydrophilic and may form solvates with water or hydrophilic organic solvents or mixtures thereof. When the resulting products are crystalline, they are purified by recrystallization. If they are non-crystalline, which is generally so, they are purified by high pressure liquid chromatography or column chromatography and/or isolated by lyophilization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), high pressure liquid chromatography (HPLC), thin layer chromatography (TLC) and/or amino acid analysis.

EXAMPLE 1

HTyrMeD-AlaNH(CH$_2$)$_3$Ph

A. ZMeD-AlaOMe

Methyl iodide (25 ml.), then sodium hydride (50% in oil, 7.2 g.), were added with stirring to a solution of N-benzyloxycarbonyl-D-alanine (11.16 g.) in tetrahydrofuran (125 ml.) and dimethylformamide (13 ml.). The mixture was then stirred under reflux for 24 hours. Water (100 ml.) was added, the pH was adjusted to 5.5 with hydrochloric acid and sodium bicarbonate, and the solvents were stripped. The residue was distributed between ether and aqueous citric acid (5%). The ether layer was washed successively with water, saturated aqueous sodium bicarbonate, water and saturated aqueous sodium chloride, then dried over sodium sulfate and stripped of ether, affording N-benzyloxycarbonyl-N-methyl-D-alanine methyl ester as a red oil (14.5 g.), which still contained the oil from the sodium hydride-oil mixture. TLC (silica gel, 3:1 hexane-ethyl acetate) of the red oil showed a single spot ($R_f \sim 0.5$).

B. HMeD-AlaOMe

A mixture of the red oil from part A of this example and hydrogen bromide in acetic acid (32%, 50 ml.) was stirred at room temperature for two hours, then stripped of volatiles. The residue was distributed between ether and water (75 ml.), and the aqueous layer was washed twice more with ether, then stripped of volatiles. After an unsuccessful attempt to crystallize the residue from methanol-ether, the methanol and ether were removed, ethanol and toluene were added, and the mixture was stripped of volatiles again. Crystallization of the residue from methanol (about 20 ml.)-ether afforded N-methyl-D-alanine methyl ester hydrobromide as white needles (7.18 g.; m.r. 116°–118° C.; $[\alpha]_D^{25}+6.0°$, c=2, dimethylformamide).

C. ZTyr(Bz)MeD-AlaOMe

Diisopropylethylamine (1.29 g.), then diphenylphosphinic chloride (2.37 g.), were added to a solution of N-benzyloxycarbonyl-O-benzyl-L-tyrosine (4.05 g.) in tetrahydrofuran (30 ml.) maintained at −20° C., and the mixture was stirred at that temperature for 10 minutes. A solution of N-methyl-D-alanine methyl ester hydrobromide (1.98 g.) in tetrahydrofuran (20 ml.) was then added, followed by diisopropylethylamine (1.29 g.). The mixture was stirred for two hours at 0° C., then overnight at room temperature, then filtered, stripped of volatiles and distributed between ethyl acetate and aqueous citric acid (5%). The ethyl acetate layer was washed with water, saturated aqueous sodium bicarbonate, water again and saturated aqueous sodium chloride, then dried over magnesium sulfate and concentrated to a yellow gum (about 6 g.). Purification of the yellow gum by high pressure liquid chromatography on silica gel (350 g.) using hexane-ethyl acetate (7:3) as the eluant afforded (N-benzyloxycarbonyl-O-benzyl-L-tyrosyl)-N-methyl-D-alanine methyl ester as a clear gum (3.2 g.) containing about a one-sixth molar amount of ethyl acetate as shown by NMR spectral analysis.

D. ZTyr(Bz)MeD-AlaNHNH$_2$

A mixture of (N-benzyloxycarbonyl-O-benzyl-L-tyrosyl)-N-methyl-D-alanine methyl ester one-sixth ethyl acetate solvate (2.8 g.), hydrazine hydrate (1.8 ml.) and methanol (50 ml.) was stirred overnight at room temperature. More hydrazine hydrate (1.8 ml.) was added and stirring was continued for another day. The volatiles were stripped, and the residue was distributed between water and ethyl acetate. The ethyl acetate layer was washed with aqueous citric acid (5%), saturated aqueous sodium bicarbonate and saturated aqueous sodium chloride, dried over magnesium sulfate, and stripped of ethyl acetate, affording (N-benzyloxycarbonyl-O-benzyl-L-tyrosyl)-N$^2$-methyl-D-alanyl hydrazide as a foam (2.5 g.).

E. ZTyr(Bz)MeD-AlaNH(CH$_2$)$_3$Ph

With cooling at ice-water temperature n-butyl nitrite (0.26 ml.), then a solution of hydrogen chloride in dimethylformamide (3.3N, 0.67 ml.), were added with stirring to a solution of (N-benzyloxycarbonyl-O-benzyl-L-tyrosyl)-N$^2$-methyl-D-alanyl hydrazide (1.01 g.) in dimethylformamide (5 ml.). After five minutes' stirring when a test for the presence of hydrazide (Hofmann et al., Journal of the American Chemical Society, vol. 85, p. 611, 1965) became negative, diisopropylethylamine (0.76 ml.), then a solution of 3-phenylpropylamine (0.30 g.) in dimethylformamide (3 ml.), were added. Stirring was continued for four hours at 0° C., and the mixture was refrigerated at about 5° C. overnight, then quenched in water. The resulting gum was extracted with ethyl acetate. The ethyl acetate extract was washed with water, aqueous citric acid (5%), water, saturated aqueous sodium bicarbonate, and saturated aqueous sodium chloride, dried over magnesium sulfate, and stripped of ethyl acetate. Crystallization of the residue from isopropyl acetate-hexane afforded (N-benzyloxycarbonyl-O-benzyl-L-tyrosyl)-N$^2$-methyl-N-(3-phenylpropyl)-D-alaninamide as white needles (800 mg., m.r. 102°–104° C.).

F. HTyrMeD-AlaNH(CH$_2$)$_3$Ph

A solution of (N-benzyloxycarbonyl-O-benzyl-L-tyrosyl)-N$^2$-methyl-N-(3-phenylpropyl)-D-alaninamide (660 mg.) in acetic acid (25 ml.) containing palladium on carbon (10%, 100 mg.) was hydrogenated under pressure (14 p.s.i.g.) for six hours, then filtered and stripped of volatiles. The residue was purified by reverse phase high pressure liquid chromatography on octadecylsilated silica gel (350 g.) using ammonium acetate (0.2%) in methanol-water (1:1) as the eluant. The product appeared centered at a k' value of 5.5. A solution of the product in methanol-water (2:1) was passed through an ion exchange resin in the dihydrogen phosphate ion form, partially stripped, diluted with water (100 ml.), partially stripped again (to 35 ml.), filtered and lyophilized, affording as an amorphous white solid L-tyrosyl-N$^2$-methyl-N-(3-phenylpropyl)-D-alaninamide phosphate salt (1:1) sesquihydrate (350 mg.), whose free base is the compound of Formula II wherein $R_1$ is hydrogen, $R_2$ is methyl and $R_4$ is $(CH_2)_nY$ wherein n is 3 and Y is phenyl.

EXAMPLE 2

MeTyrD-AlaNH(CH$_2$)$_3$Ph

A. ZMeTyr(Bz)OH

To a mixture of sodium hydride (50%, 9.64 g., prewashed with tetrahydrofuran to remove mineral oil) and tetrahydrofuran (120 ml.) were added dropwise with stirring first a filtered solution of N-benxyloxycarbonyl-O-benzyl-L-tyrosine (16.22 g.) in tetrahydrofuran (50 ml.), then methyl iodide (20 ml.), then tetrahydrofuran (10 ml.). The resulting mixture was stirred overnight at room temperature. Ethyl acetate (200 ml.) was added, then water (6 ml.) dropwise, and stirring was continued for one hour. Charcoal was added and the mixture was filtered. Water (70 ml.) and ether were added, affording a pale yellow solid which melted upon drying at 65° and resolidified upon cooling (15.72 g., m.r. 88°–90°). Recrystallization of the solid from ethyl acetate (12 ml., 5 ml. used for washing) afforded N-benzyloxycarbonyl-N-methyl-O-benzyl-L-tyrosine (14.13 g.; m.r. 90°–91.5° C.; $[\alpha]_D^{25} -54.7°$, c=1, acetic acid).

B. ZMeTyr(Bz)D-AlaOMe

A solution of isobutyl chloroformate (2.00 g.) in acetone (10 ml.) was added dropwise to a solution of N-benzyloxycarbonyl-N-methyl-O-benzyl-L-tyrosine (6.0 g.) and triethylamine (1.45 g.) in acetone (60 ml.) with stirring and cooling to −10° C. A solution of D-alanine methyl ester (2.22 g.) and triethylamine (1.45 g.) in chloroform (30 ml.) was then added. Stirring was continued for one hour at −10° C., then overnight at room temperature. The mixture was stripped of solvents. Water and ethyl acetate were added to the residue. The ethyl acetate layer was washed with water, saturated aqueous sodium bicarbonate, water again, aqueous citric acid, water again and saturated aqueous sodium chloride, dried over magnesium sulfate, filtered and stripped of ethyl acetate, affording (N-benzyloxycarbonyl-N-methyl-O-benzyl-L-tyrosyl)-D-alanine methyl ester (97% yield).

C. ZMeTyr(Bz)D-AlaNHNH$_2$

A solution of (N-benzyloxycarbonyl-N-methyl-O-benzyl-L-tyrosyl)-D-alanine (7.0 g.), hydrazine hydrate (85%, 2.5 ml.), tetrahydrofuran (50 ml.) and ethanol (20 ml.) was stirred for one hour, then allowed to stand over the weekend, at room temperature, concentrated (to about 10–15 ml.) and quenched in water. A solution of the resulting solid in tetrahydrofuran was stripped of volatiles. A solution of the resulting light yellow oil in ethyl acetate was dried over magnesium sulfate, filtered and stripped of volatiles, affording as a clear, colorless glass (N-benzyloxycarbonyl-N-methyl-O-benzyl-L-tyrosyl)-D-alanyl hydrazide (70% yield; $[\alpha]_D^{25} -43.4°$, c=1, dimethylformamide).

D. ZMeTyr(Bz)D-AlaNH(CH$_2$)$_3$Ph

By the method of part E of Example 1 (N-benzyloxycarbonyl-N-methyl-O-benzyl-L-tyrosyl)-D-alanyl hydrazide (1.51 g.) was condensed with 3-phenylpropylamine (0.406 g.), affording (N-benzyloxycarbonyl-N-methyl-O-benzyl-L-tyrosyl)-N-(3-phenylpropyl)-D-alaninamide (1.67 g.).

E. MeTyrD-AlaNH(CH$_2$)$_3$Ph

By the method of part F of Example 1 (N-benzyloxycarbonyl-N-methyl-O-benzyl-L-tyrosyl)-N-(3-phenylpropyl)-D-alaninamide was deprotected and the product was purified, affording after conversion of the phosphate salt of the product to the hydrochloride salt of the product N-methyl-L-tyrosyl-N-(3-phenylpropyl)-D-alaninamide monohydrochloride (264 mg.), whose free base is the compound of Formula II wherein R$_1$ is methyl, R$_2$ is hydrogen and R$_4$ is (CH$_2$)$_n$Y wherein n is 3 and Y is phenyl, as an amorphous amber solid.

EXAMPLE 3

MeTyrMeD-AlaNH(CH$_2$)$_3$Ph

A. ZMeD-AlaNH(CH$_2$)$_3$Ph

A solution of isobutyl chloroformate (3.75 ml.) in tetrahydrofuran (10 ml.) was added to a solution of N-benzyloxycarbonyl-N-methyl-D-alanine (6.7 g.) and triethylamine (4.04 ml.) in tetrahydrofuran (56 ml.) with stirring and cooling to −20° C. A solution of 3-phenylpropylamine (3.92 g.) in tetrahydrofuran was then added. The mixture was stirred for two hours at 0° C., then overnight at room temperature, then filtered and stripped of volatiles. The residue was distributed between ethyl acetate (100 ml.) and water (100 ml.). The ethyl acetate layer was washed with hydrochloric acid (5%), water, saturated aqueous sodium bicarbonate, water again and saturated aqueous sodium chloride, dried over magnesium sulfate and stripped of ethyl acetate. High pressure liquid chromatography of the resulting yellow oil (10.0 g.) on silica gel (350 g.) using hexane-ethyl acetate (7:3) as the eluant afforded in fractions 6–7 corresponding to k'=4 through k'=7 N$^2$-benzyloxycarbonyl-N$^2$-methyl-N-(3-phenylpropyl)-D-alaninamide (8.1 g.).

B. MeD-AlaNH(CH$_2$)$_3$Ph

A solution of N$^2$-benzyloxycarbonyl-N$^2$-methyl-N-(3-phenylpropyl)-D-alaninamide (7.54 g.) in ethanol (200 ml.) containing palladium on carbon (10%, 200 mg.) was hydrogenated under pressure (40 p.s.i.g.), filtered and stripped of volatiles, affording N$^2$-methyl-N-(3-phenylpropyl)-D-alaninamide.

C. ZMeTyr(Bz)MeD-AlaNH(CH$_2$)$_3$Ph

By the method of part C of Example 1 N-benzyloxycarbonyl-N-methyl-O-benzyl-L-tyrosine (1.65 g.) was condensed with N$^2$-methyl-N-(3-phenylpropyl)-D-alaninamide (0.88 g.), affording (N-benzyloxycarbonyl-N-methyl-O-benzyl-L-tyrosyl)-N$^2$-methyl-N-(3-phenylpropyl)-D-alaninamide as a yellow wax (1.8 g.).

D. MeTyrMe-D-AlaNH(CH$_2$)$_3$Ph

After an unsuccessful attempt to effect deprotection by catalytic hydrogenation under pressure (25 p.s.i.g.) with palladium on carbon as catalyst and acetic acid as solvent, a solution of (N-benzyloxycarbonyl-N-methyl-O-benzyl-L-tyrosyl)-N$^2$-methyl-N-(3-phenylpropyl)-D-alaninamide (1.7 g.) and hydrogen bromide in acetic acid (32%, 20 ml.) was allowed to stand at room temperature for one hour, then partially stripped of volatiles. Ether (100 ml.) was added to the residue, which was triturated three more times with ether, affording a yellow-brown oil. Upon reverse phase high pressure liquid chromatography on octadecylsilated silica gel (350 g.) using ammonium acetate (0.2%) in methanol-water (1:1) as the eluant, the product appeared in the methanol wash. Rechromatography using ammonium acetate (0.15%) in methanol-water (3:2) as the eluant and washing the residue of fractions 3–4 corresponding to k'=2.4–5.0 free of salt gave a beige gum (570 mg.). A solution of the beige gum in methanol-water (2:1) was passed through an ion exchange resin in the dihydrogen phosphate ion form, filtered and lyophilized, affording as an amorphous white solid N-methyl-L-tyrosyl-N$^2$-methyl-N-(3-phenylpropyl)-D-alaninamide phosphate (1:1) salt dihydrate (584 mg.; $[\alpha]_D^{25} +61.6°$, c=1, methanol), whose free base is the compound of Formula II wherein R$_1$ and R$_2$ are each methyl and R$_4$ is (CH$_2$)$_n$Y wherein n is 3 and Y is phenyl.

EXAMPLE 4

HTyrEtD-AlaNH(CH$_2$)$_3$Ph

A. BocEtD-AlaOH

A solution of N-(tert-butyloxycarbonyl)-D-alanine (9.46 g.) in tetrahydrofuran (75 ml.) was added dropwise with stirring to a suspension of sodium hydride (35% in oil, 17.2 g.) in tetrahydrofuran (50 ml.) containing 18-crown-6 ether (0.3 g.) maintained at ice bath temperature. Stirring was continued for 1.5 hours, then ethyl iodide (8 ml.) was added. Stirring was continued for 2.5 hours, while the temperature was allowed to rise to room temperature. First was added a mixture of tetrahydrofuran (10 ml.) and acetic acid (10 ml.), then ethanol (20 ml.). The mixture was poured into ice (400 ml.). Sufficient aqueous sodium hydroxide (2N) was added to adjust the pH to 13. The mixture was washed twice with ether (200 ml. each time), then acidified to pH 3 with solid citric acid hydrate, then extracted thrice with ether (200 ml. each time). The ethereal extracts were dried and stripped of ether. Dicyclohexylamine (9 ml.) was added to a solution of the resulting crystals (9.8 g.) in ether (150 ml.), affording N-(tert-butyloxycarbonyl)-N-ethyl-D-alanine dicyclohexylamine salt in two crops (4.61 g., m.r. 126°–128°, 2.40 g.).

B. BocEtD-AlaNH(CH$_2$)$_3$Ph

By the method of part A of Example 3 N-(tert-butyloxycarbonyl)-N-ethyl-D-alanine free base (3.9 g.) was condensed with 3-phenylpropylamine (2.4 g.), affording N$^2$-(tert-butyloxycarbonyl)-N$^2$-ethyl-N-(3-phenylpropyl)-D-alaninamide as a syrup (4.41 g.).

C. EtD-AlaNH(CH$_2$)$_3$Ph

A solution of N$^2$-(tert-butyloxycarbonyl)-N$^2$-ethyl-N-(3-phenylpropyl)-D-alaninamide (4.28 g.) in hydrogen chloride-ethyl acetate (3.9N, 35 ml.) was stirred for twenty minutes at room temperature, then concentrated. The residue was stripped of volatiles under vacuum (0.1 mm.) at room temperature, affording N$^2$-ethyl-N-(3-phenylpropyl)-D-alaninamide (3.22 g.).

D. ZTyr(Bz)EtD-AlaNH(CH$_2$)$_3$Ph

A solution of N$^2$-ethyl-N-(3-phenylpropyl)-D-alaninamide (2.71 g.), N-benzyloxycarbonyl-O-benzyl-L-tyrosine pentafluorophenyl ester (5.71 g.) and diisopropylethylamine (1.29 g.) in tetrahydrofuran (65 ml.) was stirred overnight at room temperature. Dimethylformamide (10 ml.) and more N-benzyloxycarbonyl-O-benzyl-L-tyrosine pentafluorophenyl ester (5.71 g.) were added, stirring was continued over the weekend, and the mixture was concentrated. A solution of the residual syrup in ethyl acetate was washed with water, dilute hydrochloric acid, aqueous sodium chloride, aqueous sodium hydroxide (1N, 20 ml.) and aqueous sodium chloride again, then dried and stripped of ethyl acetate. High pressure liquid chromatography of the residue (9.2 g.) on silica gel (350 g.) using hexane-ethyl acetate (55:45) as the eluant (200 ml./min.) afforded in the fractions having a k' value range of 2.5–4.5 (N-benzyloxycarbonyl-O-benzyl-L-tyrosyl)-N$^2$-ethyl-N-(3-phenylpropyl)-D-alaninamide as a syrup which crystallized (2.291 g.).

E. HTyrEtD-AlaNH(CH$_2$)$_3$Ph

A solution of (N-benzyloxycarbonyl-O-benzyl-L-tyrosyl)-N$^2$-ethyl-N-(3-phenylpropyl)-D-alaninamide (2.0 g.) in acetic acid (enough to make 50 ml. total volume) containing palladium on carbon (10%, 0.4 g.) was hydrogenated under pressure for three and one half hours, then filtered and stripped of volatiles. The residue (2.20 g.) was purified by reverse phase high pressure liquid chromatography on octadecylsilated silica gel (350 g.) using ammonium acetate (0.15%) in methanol-water (3:2) as the eluant (200 ml./min.). The residue of the fractions having a k' value range of 2.5–4.0 was washed free of salt, then dissolved in dilute hydrochloric acid (0.0936N, 33 ml.). The solution was diluted (to 55 ml.) with water and lyophilized. A solution of the product (640 mg.) in water (40 ml.) was lyophilized, affording as an amorphous off-white solid L-tyrosyl-N$^2$-ethyl-N-(3-phenylpropyl)-D-alaninamide monohydrochloride hemihydrate (510 mg.; $[\alpha]_D^{25}$ +73.2°, c=1, methanol), whose free base is the compound of Formula II wherein R$_1$ is hydrogen, R$_2$ is ethyl and R$_4$ is (CH$_2$)$_n$Y wherein n is 3 and Y is phenyl.

EXAMPLE 5

HTyrMeD-AlaNH(CH$_2$)$_3$PhCl-p

A. ZTyr(Bz)MeD-AlaNH(CH$_2$)$_3$PhCl-p

By the method of part E of Example 1 (N-benzyloxycarbonyl-O-benzyl-L-tyrosyl)-N$^2$-methyl-D-alanyl hydrazide (3.0 g.) was condensed with 3-(4-chlorophenyl)propylamine (1.24 g.). The product was purified by high pressure liquid chromatography on silica gel (350 g.) using hexane-ethyl acetate (1:1) as the eluant and then by crystallization from hexane-ethyl acetate, affording (N-benzyloxycarbonyl-O-benzyl-L-tyrosyl)-N$^2$-methyl-N-[3-(4-chlorophenyl)propyl]-D-alaninamide (1.94 g., m.r. 141°–144° C.; second crop, 730 mg.).

B. HTyrMeD-AlaNH(CH$_2$)$_3$PhCl-p

A solution of (N-benzyloxycarbonyl-O-benzyl-L-tyrosyl)-N$^2$-methyl-N-[3-(4-chlorophenyl)propyl]-D-alaninamide (1.68 g.) and hydrogen bromide in acetic acid (37%, 25 ml.) was stirred at room temperature for one hour fifteen minutes, then triturated with ether, yielding a yellow precipitate (780 mg.). The mother liquor was stripped of volatiles. The residue (600 mg.) and the yellow precipitate were combined and subjected to reverse phase high pressure liquid chromatography on octadecylsilated silica gel (350 g.) using ammonium acetate (0.2%) in methanol-water (65:35) as the eluant (200 ml./min.). An aqueous solution of the residue from fractions 3–4 was reinjected into the column, washed with water (1 l.) and eluted with methanol. A solution of the resulting colorless gum in methanol-water (2:1) was passed through an ion exchange resin in the dihydrogen phosphate ion form, concentrated and lyophilized, affording as an amorphous off-white solid L-tyrosyl-N$^2$-methyl-N-[3-(4-chlorophenyl)propyl]-D-alaninamide phosphate (2:5) salt monohydrate (466 mg.; $[\alpha]_D^{25}$ +49.5°, c=1, methanol), whose free base is the compound of Formula II wherein R$_1$ is hydrogen, R$_2$ is methyl and R$_4$ is (CH$_2$)$_n$Y wherein n is 3 and Y is 4-chlorophenyl.

EXAMPLE 6

HTyrMeD-AlaNH(CH$_2$)$_3$PhCF$_3$-p

A. ZTyr(Bz)MeD-AlaNH(CH$_2$)$_3$PhCF$_3$-p

By the method of part E of Example 1 (N-benzyloxycarbonyl-O-benzyl-L-tyrosyl)-N$^2$-methyl-D-alanyl hydrazide (3.0 g.) was condensed with 3-(4-trifluoromethylphenyl)propylamine (prepared by first condensing 4-trifluoromethylbenzaldehyde with cyanoacetic acid in refluxing toluene using a catalytic amount of ammonium acetate, then decarboxylating the resulting α-cyano-β-(4-trifluoromethylpheny)acrylic acid in refluxing pyridine, and finally hydrogenating the resulting β-(4-trifluoromethylphenyl)acrylonitrile in methanolic ammonia at room temperature and 400 p.s.i.g. pressure using Raney nickel catalyst, m.r. of hydrochloride salt 189°–191°; 1.42 g.). The product was crystallized from ethanol, affording (N-benzyloxycarbonyl-O-benzyl-L-tyrosyl)-N$^2$-methyl-N-[3-(4-trifluoromethylphenyl)propyl]-D-alaninamide (2.85 g., m.r. 120°–122° C.).

B. HTyrMeD-AlaNH(CH$_2$)$_3$PhCF$_3$-p

By the method of part B of Example 5 (N-benzyloxycarbonyl-O-benzyl-L-tyrosyl)-N$^2$-methyl-N-[3-(4-trifluoromethylphenyl)propyl]-D-alaninamide (1.5 g.) was deprotected and the product was purified, affording as an amorphous white solid L-tyrosyl-$N^2$-methyl-N-[3-(4-trifluoromethylphenyl)propyl]-D-alaninamide phosphate (4:7) salt (650 mg.; $[\alpha]_D^{25} + 56.3°$, c=1, methanol), whose free base is the compound of Formula II wherein $R_1$ is hydrogen, $R_2$ is methyl and $R_4$ is $(CH_2)_nY$ wherein n is 3 and Y is 4-trifluoromethylphenyl.

EXAMPLE 7

HTyrMeD-AlaNH(CH$_2$)$_3$PhF-p

A. BocMeD-AlaNH(CH$_2$)$_3$PhF-p

By the method of part A of Example 3 N-(tert-butyloxycarbonyl)-N-methyl-D-alanine (2.03 g.) was condensed with 3-(4-fluorophenyl)propylamine (prepared by condensing 4-fluorobenzaldehyde with cyanoacetic acid in refluxing pyridine using piperidine as catalyst and hydrogenating the resulting β-4-fluorophenyl)acrylonitrile in ethanolic ammonia under high pressure using Raney nickel catalyst, m.r. of methanesulfonate salt 129°–131° C.; 2.49 g.), affording $N^2$-(tert-butyloxycarbonyl)-$N^2$-methyl-N-[3-(4-fluorophenyl)-propyl]-D-alaninamide as a syrup (2.77g.).

B. MeD-AlaNH(CH$_2$)$_3$PhF-p

A solution of $N^2$-(tert-butyloxycarbonyl)-$N^2$-methyl-N-[3-(4-fluorophenyl)propyl]-D-alaninamide (2.77 g.) in hydrogen chloride-ethyl acetate (3.4N, 15 ml.) was stirred for thirty minutes at room temperature, then concentrated, affording $N^2$-methyl-N-[3-(4-fluorophenyl)propyl]-D-alaninamide as a crystalline solid (2.06 g., m.r. 148°–150° C.).

C. ZTyr(Bz)MeD-AlaNH(CH$_2$)$_3$PhF-p

By the method of part C of Example 1 using triethylamine instead of diisopropylethylamine N-benzyloxycarbonyl-O-benzyl-L-tyrosine (2.95 g.) was condensed with $N^2$-methyl-N-[3-(4-fluorophenyl)propyl]-D-alaninamide (2.0 g.). The product was purified by crystallization from ethyl acetate, affording (N-benzyloxycarbonyl-O-benzyl-L-tyrosyl)-$N^2$-methyl-N-[3-(4-fluorophenyl)propyl]-D-alaninamide in two crops (2.22 g., m.r. 137°–139°; 2.21 g.).

D. HTyrMeD-AlaNH(CH$_2$)$_3$PhF-p

A solution of (N-benzyloxycarbonyl-O-benzyl-L-tyrosyl)-$N^2$-methyl-N-[3-(4-fluorophenyl)propyl]-D-alaninamide (3.75 g.) in acetic acid (enough to make 100 ml. total volume) containing palladium on carbon (10%, 0.4 g.) was hydrogenated under pressure for twenty-one hours, then filtered and stripped of volatiles. The residue was purified by reverse phase high pressure liquid chromatography on octadecylsilated silica gel (350 g.) using ammonium acetate (0.25%) in methanol-water (3:2) as the eluant (200 ml./min.). The residue of the fractions having a k' value range of 2.8–3.4 was reinjected into the column, which was washed with water, and eluted with methanol. Conversion to the phosphate salt and lyophilization of the product afforded as an amorphous white solid L-tyrosyl-$N^2$-methyl-N-[3-(4-fluorophenyl)propyl]-D-alaninamide phosphate (1:1) salt monohydrate (404 mg.; $[\alpha]_D^{25} + 65.2°$, c=1, methanol), whose free base is the compound of Formula II wherein $R_1$ is hydrogen, $R_2$ is methyl and $R_4$ is $(CH_2)_nY$ wherein n is 3 and Y is 4-fluorophenyl.

BIOLOGICAL PROPERTIES OF THE COMPOUNDS

As stated above the compounds of Formula I are useful as analgesic agents. This utility has been shown by the results of testing the examples in vitro in the guinea pig ileum test. Some of the examples have also been shown to be active in vivo in the mouse acetylcholine writhing test.

Guinea Pig Ileum Test

Adult male guinea pigs (Charles River, Hartley strain) weighing 300–500 g. are decapitated, and the terminal ileum is exposed by reflecting the overlying cecum, severed at the ileocecal juncture, and removed while cutting the mesenteric attachments to avoid excessive traction on the tissue. The ileum (about 30 cm. in length) is transferred to a beaker containing warm modified Krebs-Henseleit solution (118 mM sodium chloride, 4.75 mM potassium chloride, 2.54 mM calcium chloride, 1.19 mM potassium dihydrogen phosphate, 1.2 mM magnesium sulfate, 25 mM sodium bicarbonate, 11 mM glucose, 20 $\mu$M choline chloride and 0.125 $\mu$M pyrilamine maleate). The terminal (aboral) portion (about 10 cm. in length) is discarded, and segments (3–4 cm. in length) are cut from the remainder and gently slid onto a glass rod (5–6 mm. in diameter) and arranged so that the mesenteric attachment is in a straight line. A cotton swab moistened in the solution is then carefully used to separate the longitudinal muscle from the underlying circular muscle. The longitudinal muscle and adhering myenteric plexus is then gently removed from the remaining tissue with forceps.

Strips of this prepared longitudinal muscle are mounted in a double-jacketed organ bath (5 ml.) under tension (1.0 g.), connected to isometric transducers (Grass FT 0.03), bathed in the modified Krebs-Henseleit solution described above, aerated with oxygen-carbon dioxide (95:5) and maintained at 37° C.

Stimulators (Grass S-44) are set to deliver repetitive monophasic square wave field stimulation (supramaximal voltage, 0.10 Hz., 0.25 msec. duration) through platinum ring electrodes at the top and bottom of the bath. Regular contractions of the muscle, which result from electrically-induced liberation of acetylcholine from postganglionic parasympathetic nerves, are recorded on a polygraph (Grass model 5). Following tissue equilibration (45–60 min.) and repeated washing (every 10 min.) an aqueous solution of a reference or test compound is added to the bath in a microliter volume (1.25–250 $\mu$l) and reductions in muscle twitch height are recorded. More compound can be added with (single dose method) or without (cumulative dose method) first washing the preparation.

From the results a half-maximal inhibitory concentration (IC50) value for the compound is computed by regression analysis of a linear plot of logarithm of concentration against percent of inhibition of twitch height (probits). The ratio of the IC50 value of a reference compound to that of a test compound tested in the same preparation is the molar potency ratio. Usually four preparations are tested simultaneously by the same person (N=4), and the resulting four molar potency ratios are averaged.

The following results were obtained using the examples as test compounds and Met$^5$-enkephalin as the reference compound.

| Compound | Average Molar Potency Ratio |
| --- | --- |
| Met$^5$-enkephalin | 100 |
| Example 1 | 293 |
| Example 2 | 194 |
| Example 3 | 200 |

| Compound | Average Molar Potency Ratio |
| --- | --- |
| Example 4 | 12 |
| Example 5 | 51 |
| Example 6 | 13 |
| Example 7 | 178 |

Mouse Acetylcholine Writhing Test

Male Swiss-Webster mice each weighing 18–24 g. are treated subcutaneously (10 ml./kg. injection volume) or orally with the test compound in an aqueous vehicle. Twenty minutes thereafter each mouse is injected intraperitoneally with acetylcholine (3.2 mg./kg.) in aqueous sodium chloride (0.9%). This dose of acetylcholine causes one or more characteristic writhes in the two minute period following injection in control mice which receive the aqueous vehicle not containing the test compound. A mouse not exhibiting the writhe during the two minute period is scored inhibited by the test compound. Test compounds are screened at doses of 100 and 30 mg./kg. subcutaneously and 300 and 100 mg./kg. orally using 15 mice at each dose level. ED50 values for active compounds are estimated by probit analysis of quantal scores at four or more dose levels using 15 mice at each dose level.

The compound of Example 1 showed a subcutaneous ED50 value of 5.5 mg./kg. with 95% confidence limits of 2.6–11 mg./kg. in this test. For the compound of Example 3 similarly tested the ED50 value was 9.4 (6.7–14) mg./kg. An approximate ED50 value of <30>10 mg./kg. was obtained for the compound of Example 2 similarly tested.

To carry out the method of use and pharmaceutical composition aspects of the invention the compounds of Formula I can be administered orally or parenterally in liquid or solid dosage form as solutions, suspensions, emulsions, capsules or tablets, which are prepared with conventional pharmaceutical vehicles and adjuncts by conventional pharmaceutical techniques.

I claim:

1. 2-(L-$N^2$-$R_1$N-$R_2$-tyrosylamino)-2-$R_3$N-$R_4$-acetamide having the structural formula

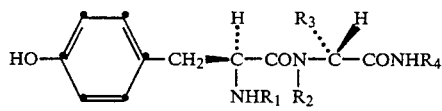

wherein
$R_1$ is hydrogen or methyl; and
$R_2$ is hydrogen or methyl; provided that at least one of $R_1$ and $R_2$ is other than hydrogen;
$R_3$ is alkyl of one to five carbon atoms; and
$R_4$ is $(CH_2)_nY$, wherein n is an integer from 2 through 10 and Y is phenyl or phenyl substituted by fluoro; or a pharmaceutically acceptable acid addition salt thereof.

2. A compound according to claim 1 wherein $R_3$ is methyl and having the structural formula

or a pharmaceutically acceptable acid addition salt thereof.

3. A compound according to claim 2 wherein $R_4$ is $(CH_2)_nY$ wherein n is 3 or a pharmaceutically acceptable acid addition salt thereof.

4. A compound according to claim 3 wherein Y is phenyl or a pharmaceutically acceptable acid addition salt thereof.

5. A compound according to claim 4 wherein $R_1$ is hydrogen or a pharmaceutically acceptable acid addition salt thereof.

6. The compound according to claim 5 wherein $R_2$ is methyl or a pharmaceutically acceptable acid addition salt thereof.

7. L-Tyrosyl-$N^2$-methyl-N-(3-phenylpropyl)-D-alaninamide phosphate (1:1) salt sesquihydrate according to claim 6.

8. A compound according to claim 4 wherein $R_1$ is methyl or a pharmaceutically acceptable acid addition salt thereof.

9. The compound according to claim 8 wherein $R_2$ is hydrogen or a pharmaceutically acceptable acid addition salt thereof.

10. N-Methyl-L-tyrosyl-N-(3-phenylpropyl)-D-alaninamide monohydrochloride according to claim 9.

11. The compound according to claim 8 wherein $R_2$ is methyl or a pharmaceutically acceptable acid addition salt thereof.

12. N-Methyl-L-tyrosyl-$N^2$-methyl-N-(3-phenylpropyl)-D-alaninamide phosphate (1:1) salt dihydrate.

13. A compound according to claim 3 wherein $R_1$ is hydrogen or a pharmaceutically acceptable acid addition salt thereof.

14. A compound according to claim 13 wherein $R_2$ is methyl or a pharmaceutically acceptable acid addition salt thereof.

15. The compound according to claim 14 wherein Y is 4-fluorophenyl or a pharmaceutically acceptable acid addition salt thereof.

16. L-Tyrosyl-$N^2$-methyl-N-[3-(4-fluorophenyl)propyl]-D-alaninamide phosphate (1:1) salt monohydrate according to claim 15.

17. The method of producing analgesia in a mammal in pain which comprises administering to the mammal an analgesically effective amount of 2-(L-$N^2$-$R_1$-N-$R_2$-tyrosylamino)-2-$R_3$-N-$R_4$-acetamide according to claim 1 or a pharmaceutically acceptable acid addition salt thereof.

18. A pharmaceutical composition for producing analgesia in a mammal consisting essentially of an analgesically effective concentration of 2-(L-$N^2$-$R_1$-N-$R_2$-tyrosylamino)-2-$R_3$-N-$R_4$-acetamide according to claim 1 or a pharmaceutically acceptable acid addition salt thereof and a pharmaceutically acceptable vehicle.

* * * * *